United States Patent
Olson et al.

(10) Patent No.: US 6,317,625 B1
(45) Date of Patent: *Nov. 13, 2001

(54) METHOD AND APPARATUS FOR INCREASING THE LOW FREQUENCY DYNAMIC RANGE OF A SYSTEM FOR MEASURING PHYSIOLOGICAL SIGNALS WITH AN IMPLANTABLE MEDICAL DEVICE

(75) Inventors: Dana J. Olson, Kirkland; David W. Van Ess, Arlington, both of WA (US); Robert W. Stadler, Shoreview; Steven N. Lu, Fridley, both of MN (US); Jeffrey D. Wilkinson, Vadnais Heights; Tara N. Ptak, Minneapolis, both of MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/713,455

(22) Filed: Nov. 15, 2000

Related U.S. Application Data

(63) Continuation-in-part of application No. 09/232,044, filed on Jan. 15, 1999.

(51) Int. Cl.$^7$ .................................................. A61B 5/0402
(52) U.S. Cl. ........................................... 600/509; 128/902
(58) Field of Search ................................. 607/5; 600/509; 128/901, 902

(56) References Cited

U.S. PATENT DOCUMENTS

| | | |
|---|---|---|
| 4,556,063 | 12/1985 | Thompson et al. . |
| 5,331,966 | 7/1994 | Bennett et al. . |
| 5,954,660 | 9/1999 | Legay et al. .......................... 600/509 |
| 6,128,526 | 10/2000 | Stadler et al. . |

OTHER PUBLICATIONS

Vanderkooy et al., "Resolution Below the Least Significant Bit in Digital Systems with Dither," *J. Audio Eng. Soc.*, vol. 32, No. 3, pp. 106–113 (Mar. 1984).

*Primary Examiner*—Jeffrey R. Jastrzab
(74) *Attorney, Agent, or Firm*—Beth L. McMahon

(57) ABSTRACT

A signal measuring system for use with an Implantable Medical Device (IMD) is provided for measuring physiologic signals having a relatively large effective dynamic range. In one embodiment, the system includes a High-Pass Filter (HPF), an Analog-to-Digital Converter (ADC), a Decimation Filter (DF), and a Compensation Filter (CF). The HPF receives an input signal that includes both the baseline wander imposed on a physiological signal. According to one aspect of the invention, the HPF attenuates low frequency components of the input signal, including a portion of the frequency band within the desired output signal bandwidth. The ADC then oversamples the output signal of the HPF. The DF receives the output samples from the ADC and generates output samples at rate that is at least twice the maximum frequency of the desired output signal. The CF then amplifies the low frequency end of the DF output samples. The gain and cutoff frequency of the CF are selected to offset the HPF attenuation of those low frequency components of the input signal below the cutoff frequency of the HPF and above the minimum frequency of the desired output signal. In one embodiment, the DF and CF are implemented by a processing circuit executing programmed instructions. The processing circuit may be included within the IMD, or may be partially or fully implemented within a device that is external to the IMD.

43 Claims, 9 Drawing Sheets

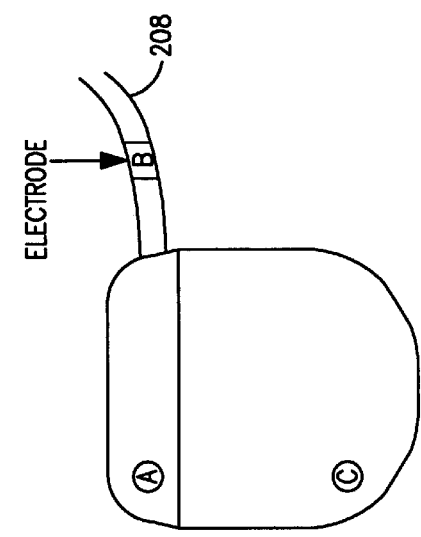
FIG. 13A
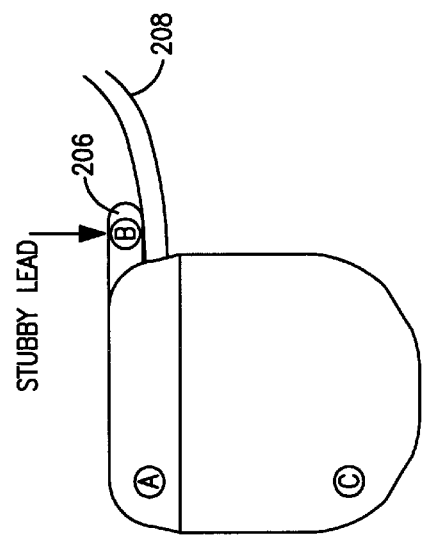
FIG. 13B
FIG. 13C
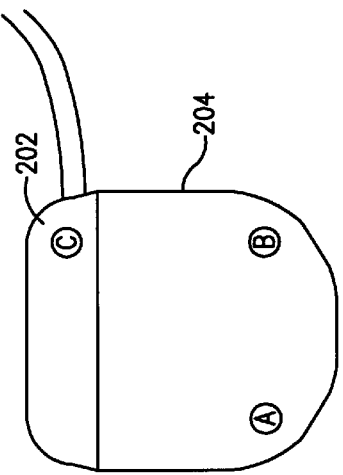
FIG. 13D
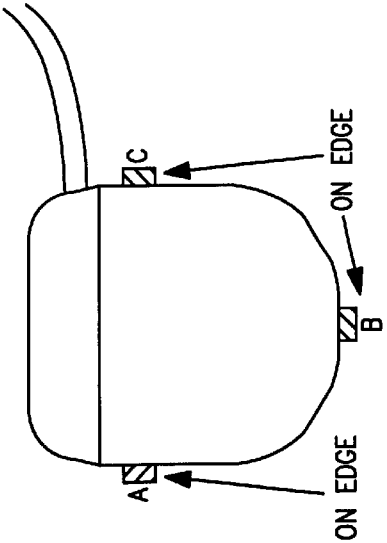
FIG. 13E Time (sec) ⟶

METHOD AND APPARATUS FOR INCREASING THE LOW FREQUENCY DYNAMIC RANGE OF A SYSTEM FOR MEASURING PHYSIOLOGICAL SIGNALS WITH AN IMPLANTABLE MEDICAL DEVICE

The current application is a continuation-in-part of U.S. Patent Application entitled "Method and Apparatus for Increasing the Low Frequency Dynamic Range of a Digital ECG Measuring System", Ser. No. 09/232,044 filed Jan. 15, 1999 incorporated herein by reference in its entirety.

FIELD OF THE INVENTION

The present invention relates to system for use within an Implantable Medical Device for measuring physiological signals using analog-to-digital processing; and, more specifically, relates to a system for increasing the dynamic frequency range of signals that can be measured within a patient's body.

BACKGROUND INFORMATION

Many Implantable Medical Devices (IMDs) measure physiological parameters of a patient's body. These signals may be used for diagnosis, and to enable a physician to render appropriate treatment. Examples of physiologic parameters measured by an IMD may include body temperature and pressure, tissue impedance, and tissue oxygen levels. As another example, it is often desirable to measure a voltage existing between two points in the body. This measurement is typically obtained between two electrodes.

Many types of IMDs obtain voltage measurements for use in the diagnosis and treatment of medical conditions. For example, pacemakers, defibrillators, cardioverters, and hemodynamic monitors often measure electrocardiograms (EGMs), which are voltage signals measured within a patient's cardiovascular system and used in the diagnosis and treatment of heart conditions. These signals may be transferred immediately to external devices for use in diagnosis, or may be temporarily stored in the IMD and transferred for later external use. These signals may also be used by the IMD to adjust treatment.

One problem with obtaining accurate voltage measurements within a patient's body involves baseline wander. Baseline wander involves large amplitude, low-frequency, non-physiological signals that can saturate a measurement system, resulting in the loss of patient signal information. There are several sources of baseline wander that often affects internal devices. Patient movement, for example, may disturb the electrical connection of an electrode, causing a low frequency signal to be superimposed on the physiologic signal. Another source of baseline wander in pacing devices, cardioverters, and defibrillators, involves the delivery of electrical stimulus to tissue in the region of the electrode. This delivery of electrical energy creates an electrical field that interferes with the physiological signal being measured.

FIG. 2 shows how baseline wander can affect the measurement of a physiological signal such as an EGM. In FIG. 2, an initial portion 21 of curve 20 has a relatively large rate of change as will occur upon delivery of electrical stimulus to tissue surrounding an electrode. The bias current signal eventually begins to stabilize, as indicated by a portion 23 of curve 20. The bias current signal results in a significant rate of change of the combined input signal, wherein the combined signals include the baseline wander imposed on the physiological signal being measured. This rate of change of the combined input signal is referred to herein as the slew rate. When the bias current signal eventually starts to stabilize, the slew rate of the combined input signal is reduced.

Conventional techniques can be used to compensate for the "offset" caused by the baseline wander in order to keep the combined input signal from saturating the system. However, conventional compensation techniques are generally inadequate for the high slew rate of the combined signal caused during the initial period of the bias current signal as discussed above. Additionally, when conventional techniques are used to compensate for the offset, the waveform morphology is changed. This change makes patient diagnosis and monitoring more difficult. For example, by using a conventional filter having a cut-off frequency selected to remove the offset resulting from baseline wander, waveform characteristics used to diagnose ischemia are filtered from the measured signal.

FIG. 3 is a block diagram illustrative of conventional digital signal measuring system of the type that may be used to measure a physiological signal. Signal measuring system 10 includes a preamplifier 31, a high pass filter (HPF) 33, an analog-to-digital converter (ADC) 35 and a second HPF 37. As will be appreciated by those skilled in the art, signal measuring system 10 includes an anti-aliasing filter (not shown) configured to filter out frequency components of the input signal above one-half of the sample rate of ADC 35.

In this example, the passband of HPF 33 is set at about 0.03 Hz, while the passband of HPF 37 is set at about 0.02 Hz. This gives a passband with a lower edge of 0.05 Hz. This performance is consistent with industry standards for diagnostic quality surface electrocardiograms. Unfortunately, the baseline wander signal has frequency components above 0.05 Hz. Thus, in this example, HPF 33 passes the baseline wander signal along with the input signal to cause the saturation problem described above.

One conventional solution to this problem is to increase the dynamic range of the system. Current industry standards require a dynamic range of at least 10 mV (i.e. ranging from ±5 mV). Diagnostic and interpretive algorithms require resolution of 5.0 $\mu$V. This range is adequate for physiological signals that do not include baseline wander. Sources of baseline wander discussed above dictate that the dynamic range would have to be increased to greater than 150 mV. However, to increase the dynamic range and maintain a given resolution would require an increase in the number of bits of the analog-to-digital conversion. For example, a twelve-bit ADC can be used for 20 mV dynamic range and 5 $\mu$V resolution. However, a sixteen-bit ADC may be required for 160 mV dynamic range and the same 5 $\mu$V resolution. The cost of a sixteen-bit ADC is significantly higher than a twelve-bit ADC, which undesirably increases the cost of the signal measuring system. In addition, a sixteen-bit ADC utilizes more power than a twelve or eight-bit ADC. This is undesirable in the context of an Implantable Medical Device (IMD) wherein power conservation is a primary design consideration.

Another solution to a related problem of measuring an external electrocardiograph (ECG) signal is disclosed in co-pending and commonly assigned U.S. patent application Ser. No. 09/013,570, entitled "Digital Sliding Pole Fast Restore For An Electrocardiograph Display," Stice, et al. Although the disclosed digital sliding pole invention represents a substantial improvement over the prior art, further improvement is, of course, generally desirable. Thus, there is a need for a low-cost, energy-efficient, physiological signal measuring system for use in an IMD having a relatively large dynamic range and high resolution. The system should minimize the changes in the morphology of the physiological signal being measured so that the ability to provide accurate patient diagnoses is not compromised.

SUMMARY

In accordance with the present invention, a signal measuring system for an IMD is provided for measuring physiologic signals having a relatively large effective dynamic range. This system is adaptable for use in measuring electrocardiograms. In one aspect of the present invention, low frequency compression/enhancement techniques are combined with dither techniques to effectively increase the dynamic range while maintaining resolution. This aspect of the present invention is achieved without increasing the number of bits of the ADC that is used to convert the sensed signal to digital format.

In one embodiment, the system includes a HPF, an ADC, a decimation filter (DF), and a compensation filter (CF). The HPF receives an input signal that includes the baseline wander imposed on the physiological signal. The HPF attenuates the low frequency components of the input signal. Unlike conventional systems, the HPF serves to attenuate the bias current signal so that the sampled signal remains within the dynamic range of the system. In one embodiment, the HPF attenuates frequency components that are within the frequency bandwidth of the desired output signal. The ADC then oversamples the output signal of the HPF. The DF receives the output samples of the ADC and generates output samples at a rate that is at least twice the maximum frequency of the desired output signal. The CF then amplifies the low frequency end of the DF output samples. The gain and cutoff frequency of the CF are, ideally, set to substantially offset the attenuation of the HFP for those low frequency components of the input signal below the cutoff frequency of the HPF and above the minimum frequency of the desired output signal. Although it would appear that the resolution of these low frequency components has been degraded, dither techniques are used, in effect, to exchange sample rate for resolution. In one embodiment, system noise (noise inherent in the system due to imperfections in the components, thermal noise, etc.) is used as the dither. As a result of the compression/enhancement and dither techniques, the output signal remains within the dynamic range of the system with the desired resolution, which allows the system to display an accurately measured signal significantly faster than conventional systems.

The low frequency compression/enhancement techniques used by the present invention allow the morphology of the waveform to be retained. Thus, unlike conventional systems that remove important low-frequency components from the waveform, making conditions such as ischemia difficult, if not impossible, to diagnose, the current system generates waveform data that includes important low-frequency information needed to make an accurate diagnosis.

BRIEF DESCRIPTION OF THE DRAWINGS

The foregoing aspects and many of the attendant advantages of this invention will become more readily appreciated by reference to the following detailed description, when taken in conjunction with the accompanying drawings listed below.

FIGS. 13A through 13E are diagrams illustrating various configurations of subcutaneous electrodes positioned adjacent to the housing of an IMD used in conjunction with the current invention.

DETAILED DESCRIPTION

Figure 4:
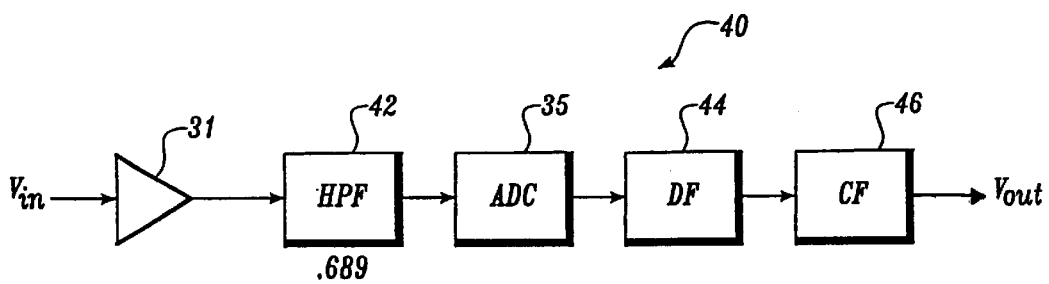
FIG. 4 is a block diagram illustrative of a digital signal measuring system according to one embodiment of the present invention.

FIG. 4 is a block diagram illustrative of a digital signal measuring system 40, according to one embodiment of the present invention. For exemplary purposes, this system will be described in terms of measuring cardiac signals, although it will be understood this system could be equally adapted for measuring voltage potentials anywhere internal to, or external to, a body. For clarity, the same reference numbers are used in the figures to indicate elements having the same or similar structure or function. In this embodiment, signal measuring system 40 includes preamplifier 31, a HPF 42, an anti-aliasing filter (AAF) 48, ADC 35, a decimation filter (DF) 44, and a compensation filter (CF) 46.

Figure 1:
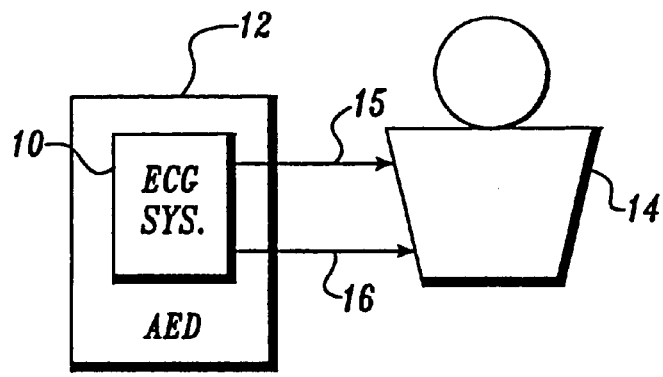
FIG. 1 is a diagram illustrative of a typical signal measuring system.
Figure 2:
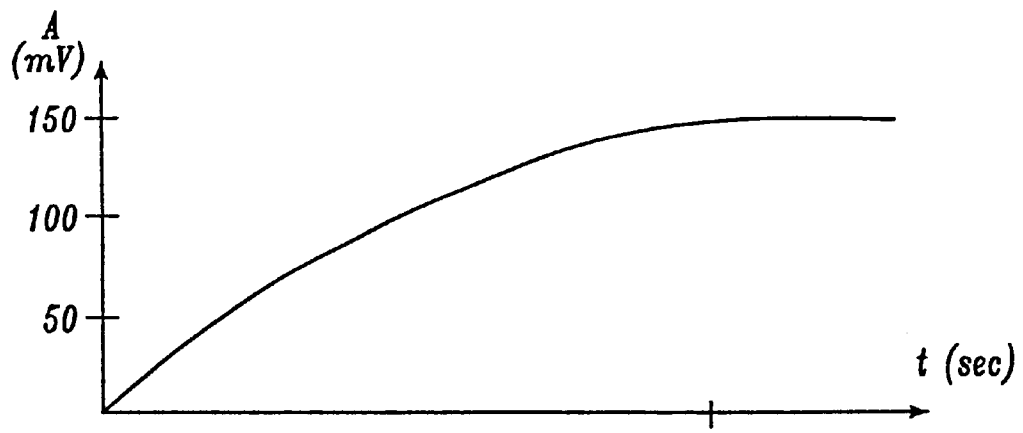
FIG. 2 is a graph illustrative of an generated by a conventional signal measuring system in applying electrodes to a patient.
Figure 3:
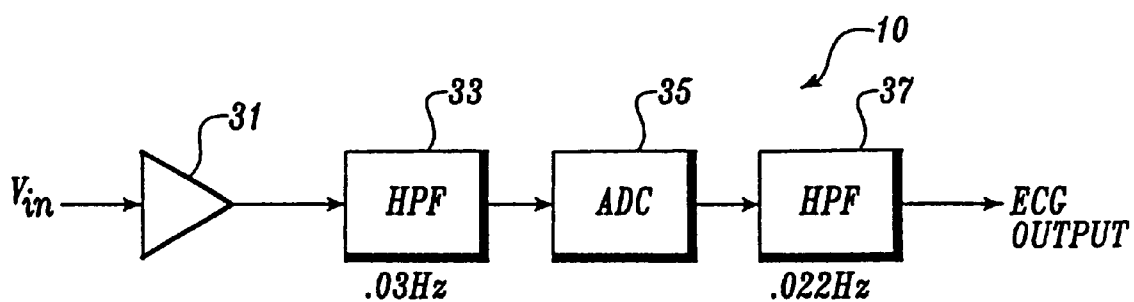
FIG. 3 is a block diagram illustrative of a conventional digital signal measuring system.
Figure 5:
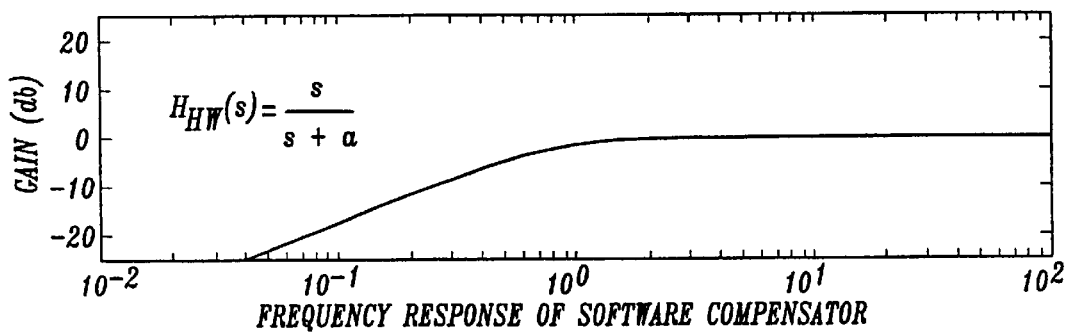
FIG. 5 is a graph illustrative of the frequency response of the high pass filter depicted in FIG. 4, according to one embodiment of the present invention.

Measuring system 40 is interconnected as follows. Preamplifier 31 is connected to receive the combined input signal via electrodes 15 and 16 (FIG. 1). In one embodiment, anti-aliasing filter (typically a LPF having a cutoff frequency less than one half of the sampling rate of the ADC) receives the output signal of preamplifier 31. Alternatively, anti-aliasing filter 48 can be placed anywhere in the signal processing flow before ADC 35, or removed entirely if frequency aliasing is not a concern. HPF 42 is connected to receive the output signal of anti-aliasing filter 48. In this embodiment, HPF 42 has a cutoff frequency of about 0.689 Hz. The frequency response of HPF 42 is illustrated in FIG. 5. In this embodiment, anti-aliasing filter 48 and HPF 42 are respectively implemented in hardware as a 3rd order Butterworth analog filter and a first order analog filter.

Referring back to FIG. 4, ADC 35 is connected to receive the output signal of HPF 42. In this embodiment, ADC 35 is implemented using a twelve-bit ADC, such as, for example, a model AD7892 available from Analog Devices, Norwood, Mass., with a 5 kilo samples-per-second (ksps) sampling rate on each of a large number of sequentially selected channels. Those skilled in the art will appreciate that the ADC selected need not be a twelve-bit device and many other ADC devices could be used. For an input signal with a 20 mV dynamic range, twelve-bit ADC 35 will generate a digital output signal with 5 $\mu$V resolution (i.e., a uniform 5 $\mu$V step size).

DF 44 is shown connected to receive the output samples from ADC 35. DF 44 may be implemented in software, firmware, or hardware as a 61-tap low-pass finite impulse response (FIR) filter. In one embodiment, DF 44 computes a weighted running average of the ADC output samples, filters out the frequency components above 150 Hz, and outputs a 0.5 ksps data stream. In this embodiment, the decimation is performed by shifting the 5 ksps weighted running average samples into a shift register and selecting every tenth sample shifted out of the shift register to serve as the DF output data stream. In yet another embodiment, DF is omitted entirely from the current invention.

Figure 6:
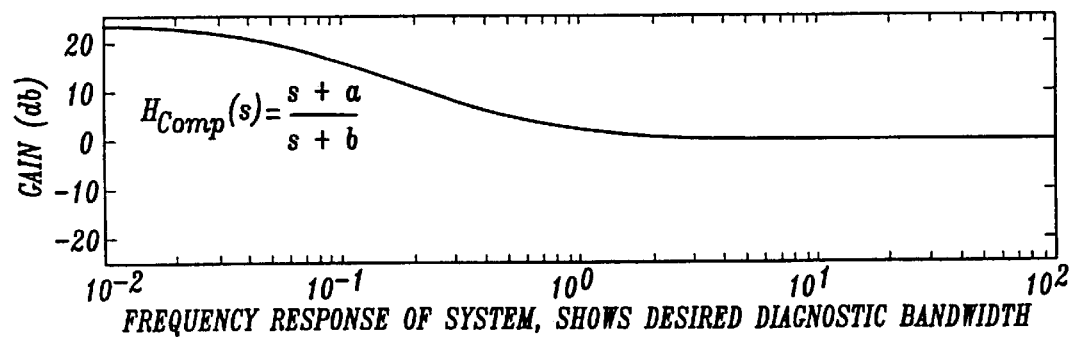
FIG. 6 is a graph illustrative of the frequency response of the compensation filter depicted in FIG. 4, according to one embodiment of the present invention.
Figure 7:
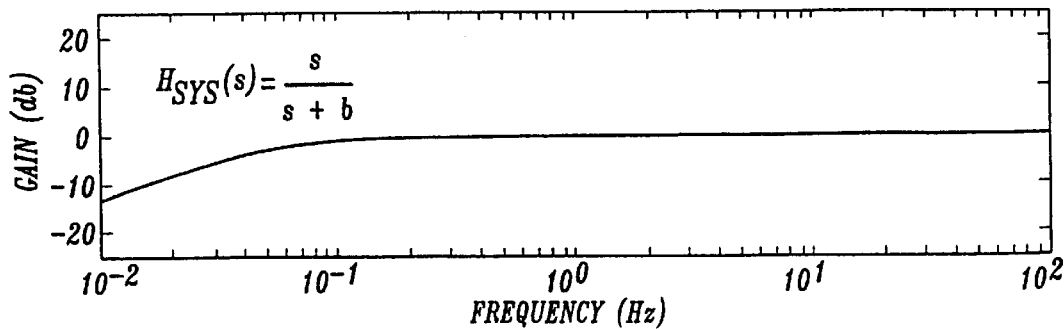
FIG. 7 is a graph illustrative of the frequency response of the system depicted in FIG. 4, according to one embodiment of the present invention.

CF 46 is connected to receive the output data stream from DF 44. CF 46 is implemented in software as a low pass digital filter with amplification or scaling of the output data stream. In this embodiment, the transfer function of CF 46 has a pole equal to the lower frequency boundary of the desired ECG output signal bandwidth (e.g., 0.05 Hz) and has a zero equal to the pole of HPF 42. The frequency response of CF 46 is illustrated in FIG. 6. Consequently, the frequency response of HPF 42 cascaded with CF 46 is equivalent to a LPF having a pole at the lower frequency boundary of the desired output signal bandwidth as illustrated in FIG. 7. The implementation of the CF in software is discussed further below in reference to FIG. 12.

Referring back to FIG. 4, signal measuring system 40 operates as follows. Preamplifier 31 receives the combined input signal from electrodes 15 and 16 (FIG. 1). In this embodiment, the combined input signal has been filtered through AAF 48. HPF 42 then filters the amplified combined input signal outputted by preamplifier 31. In this embodiment, HPF 42 filters out frequency components of the amplified combined input signal below 0.689 Hz. A more specific statement of the operation of HPF 42 is:

$$H_{HPF}(\omega) = \frac{s}{(s+a)} \quad (1)$$

where $H_{HPF}{}^{(\omega)}$ is the frequency response of HPF 42 and the variable "a" is the cutoff frequency of HPF 42 in radians. As will be appreciated by those skilled in the art, "a" is set to a frequency to attenuate the aforementioned baseline wander signal to prevent saturation of ADC 35. In the above embodiment, "a" is equal to about 2(0.689)π. In many signal measuring systems that conform to current industry standards for measuring cardiac signals, "a" is greater than the required lower frequency boundary of the output signal. Consequently, at this point of the signal processing, preventing saturation of ADC 35 comes at the cost of undesirably attenuating the lower frequency portion of the desired output signal.

ADC 35 then samples the output signal from HPF 42. In this embodiment, ADC 35 samples at a rate of about 5 ksps, which is significantly greater than twice the maximum frequency boundary of the desired signal band. Because HPF 42 attenuates the baseline wander signal, the signal received by ADC 35 has a dynamic range no greater than 20 mV, thereby preventing saturation of ADC 35. DF 44 then, as described above, low pass filters and reduces the sampling rate of the digital signal generated by ADC 35 to about 0.5 ksps.

CF 46 then, as described above, filters the output data stream from DF 44 to compensate for the attenuation of the signal frequency components below the cutoff frequency of HPF 42 and above the minimum frequency boundary of the desired signal band. This frequency band is referred to herein as the low-end band. In this embodiment, CF 46 provides a gain that is the inverse of the attenuation of the low-end band, which in this case is between 0.05 Hz and 0.689 Hz. A more specific statement of the operation of CF 46 is:

$$H_{CF}(\omega) = \frac{(s+a)}{(s+b)} \quad (2)$$

where $H_{CF}{}^{(\omega)}$ is the frequency response of CF 46, the variable "b" is the desired low frequency boundary in radians of the output signal, and variable "a" is as defined above in definition (1). In the above embodiment, "b" is equal to about 2(0.05)π. Accordingly, the transfer function of HPF 42 cascaded with CF 46 is:

$$H_{SYS}(\omega) = \frac{s}{(s+b)} \quad (3)$$

where $H_{SYS}{}^{(\omega)}$ is the frequency response of HPF 42 cascaded with CF 46, and the variable "b" is as defined above in definition (2). It might appear that this compensation by CF 46 degrades the resolution of the system because the scaling of the low-end band also scales the step size. For example, if CF 46 amplifies a certain portion of the low-end band by ten, then the resolution of that portion would appear to be 25 $\mu$V. However, the inventors of the present invention have observed that the essentially random system or thermal noise injected into the combined input signal before ADC 35 has an average level greater than the step size or resolution of ADC 35. Thus, the system noise is, in effect, a dither signal that improves resolution by modulating some of the quantization error outside the frequency band of interest. In this way, dither techniques can be used to improve resolution below the least significant bit (e.g., see Vanderkooy and Lipshitz, "Resolution Below the Least Significant Bit it Digital Systems with Dither," J. Audio Eng. Soc., Vol. 32, No. 3, March, 1984, pp. 106–112). The output data stream of CF 48 is then displayed in analog form using conventional circuitry.

In light of this disclosure, those skilled in the art of sample data systems typified by signal measuring systems will appreciate that dither techniques can improve the resolution beyond the improvement provided by oversampling alone. For example, oversampling provides about a half bit of increased resolution for each doubling of the sampling frequency. Thus, using oversampling alone would require an oversample ratio of about 256, resulting in a minimum sample rate of about 76.8 ksps to achieve four-bit resolution improvement. However, it can be shown that because the de-emphasis and enhancement is performed only on the low-end band, the oversampling ratio required to achieve the desired resolution is more strongly dependent on variable "b" rather than the upper frequency boundary of the desired output signal. In particular, the desired resolution can be achieved by ensuring that the oversampling ratio is at least equal to:

$$1 + \frac{a^2}{b \cdot \omega_{upper}} \tag{4}$$

where $\omega_{upper}$ represents the upper frequency boundary in radians of the desired output signal. This ensures that the quantization noise power is equivalent to that of a system which does not have the low-end frequency compensation. Thus, to achieve a resolution within 5 $\mu$V using the present invention, a minimum oversample ratio of about 1.06 is required, resulting in minimum sample rate of about 0.318 ksps. The 0.5 ksps data stream provided by DF 44 exceeds the required sample rate. There may be a system situation where a higher frequency "a" is required to maintain the desired dynamic range. In this case the oversampling rate is increased. For example with a HPF frequency of 5.0 Hz, the oversampling rate is calculated to be 4.33, resulting in a minimum sample rate of about 2.15 kHz.

Figure 8:
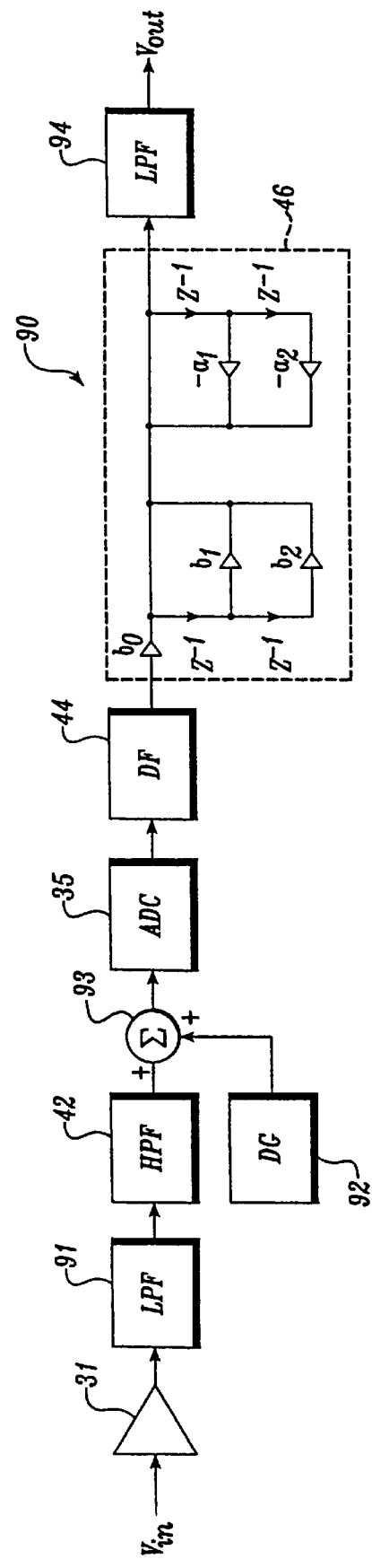
FIG. 8 is a block diagram illustrative of a digital signal measuring system, according to another embodiment of the present invention.

FIG. 8 is a block diagram illustrative of a digital signal measuring system 90, according to another embodiment of the present invention. Measuring system 90 is similar to signal measuring system 40 (FIG. 4) except that signal measuring system 90 shows the anti-aliasing filter as a LPF 91, and includes a dither generator (DG) 92, a hardware summer or combiner 93 and a LPF 94. DG 92 can be implemented with any suitable conventional signal generator. CF 46 may be implemented in software, firmware, or hardware as a standard biquad digital filter which utilizes summers, delays and multipliers.

Signal measuring system 90 is interconnected as follows. Preamplifier 31 is connected to receive the combined signal. LPF 91, functioning as an AAF, is connected to received the output signal from preamplifier 31 and provide its filtered output signal to HPF 42. Combiner 93 is connected to sum the output signal from HPF 42 and DG 92. ADC 35 is connected to receive the output signal from combiner 93 and provide its output samples to DF 44. CF 46 is connected to receive the data stream from DF 44. CF 46 then provides its output data stream to LPF 94. The output data stream of LPF 94 is then processed by conventional circuitry (not shown) to generate the measured signal value.

This embodiment of CF 46 is a standard two tap IIR filter with a Direct Form I structure that may be efficiently implemented in software, firmware, or hardware. The transfer function of this filter is equivalent to that of definition (2). Another advantage of the embodiment of CF 46 is that the effective pole and zero of CF 46 can be easily changed "on-the-fly" by modifying calculation coefficients without inducing transients in the output of the filter. This allows operation of a fast restore function for baseline initialization after external transient events such as a defibrillation pulse.

Signal measuring system 90 operates essentially as described above for signal measuring system 40 (FIG. 4) except that DG 92 adds a predetermined dither signal (e.g., a triangular wave with varying between ±one half of the step size of ADC 35) instead of relying on system noise. This embodiment may be advantageously used in applications in which the system noise is small relative to the step size of the ADC. However, when DG 92 is configured to generate a known periodic dither signal, the dither signal can be used to shift the quantization noise out of the frequency range of interest.

LPF 94 is used to filter out the repeated or harmonic spectrums caused by the operation of the digitization process on the dithered signal. In addition, those skilled in the art will appreciate that interchanging the order of processing by DF 44 and CF 46 does not change the system response. Changing the order of processing in this manner would, however, increase the complexity and computing burden of the compensation filter by the ratio of the decimation.

Figure 9:
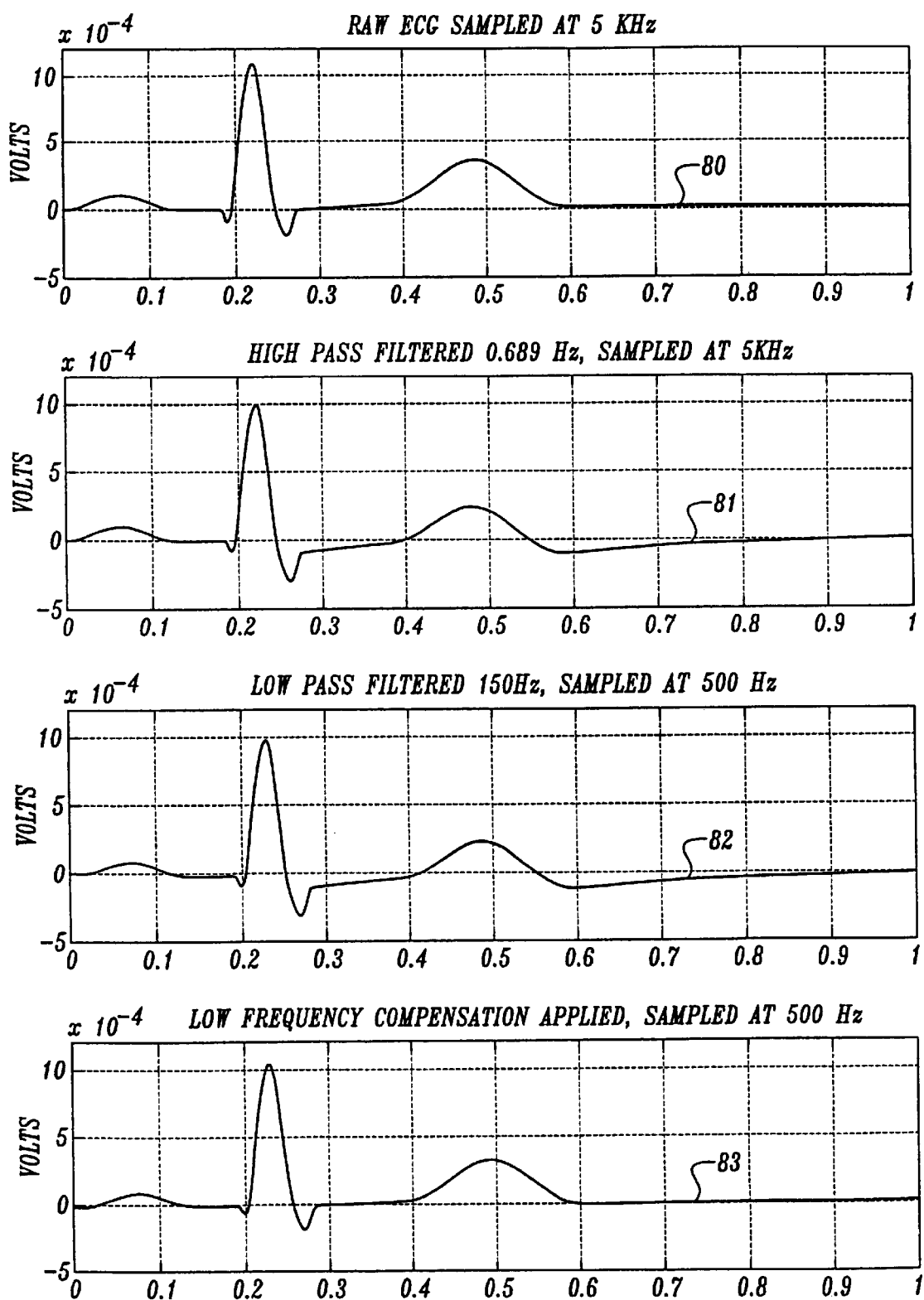
FIG. 9 is a graph illustrative of the waveforms generated by the signal measuring system of FIG. 9.

FIG. 9 shows the waveforms generated by a simulation of a signal measuring system 90. The input signal data is shown as sampled at 5 ksps as a waveform 80. The output signal generated from HPF 42, set in this example at 0.689 Hz is shown as a waveform 81. Waveform 81 has a significant droop in slow moving parts of the waveform as is expected from a HPF with corner frequency in the band of interest. Decimation is accomplished in DF 44 which provides 150 Hz LPF at 500 sps shown as a waveform 82. The output signal generated from CF 46, shown as a waveform 83, is clearly nearly identical to the raw input waveform 80, maintaining the fidelity required for diagnostic interpretation of the signals.

Figure 10:
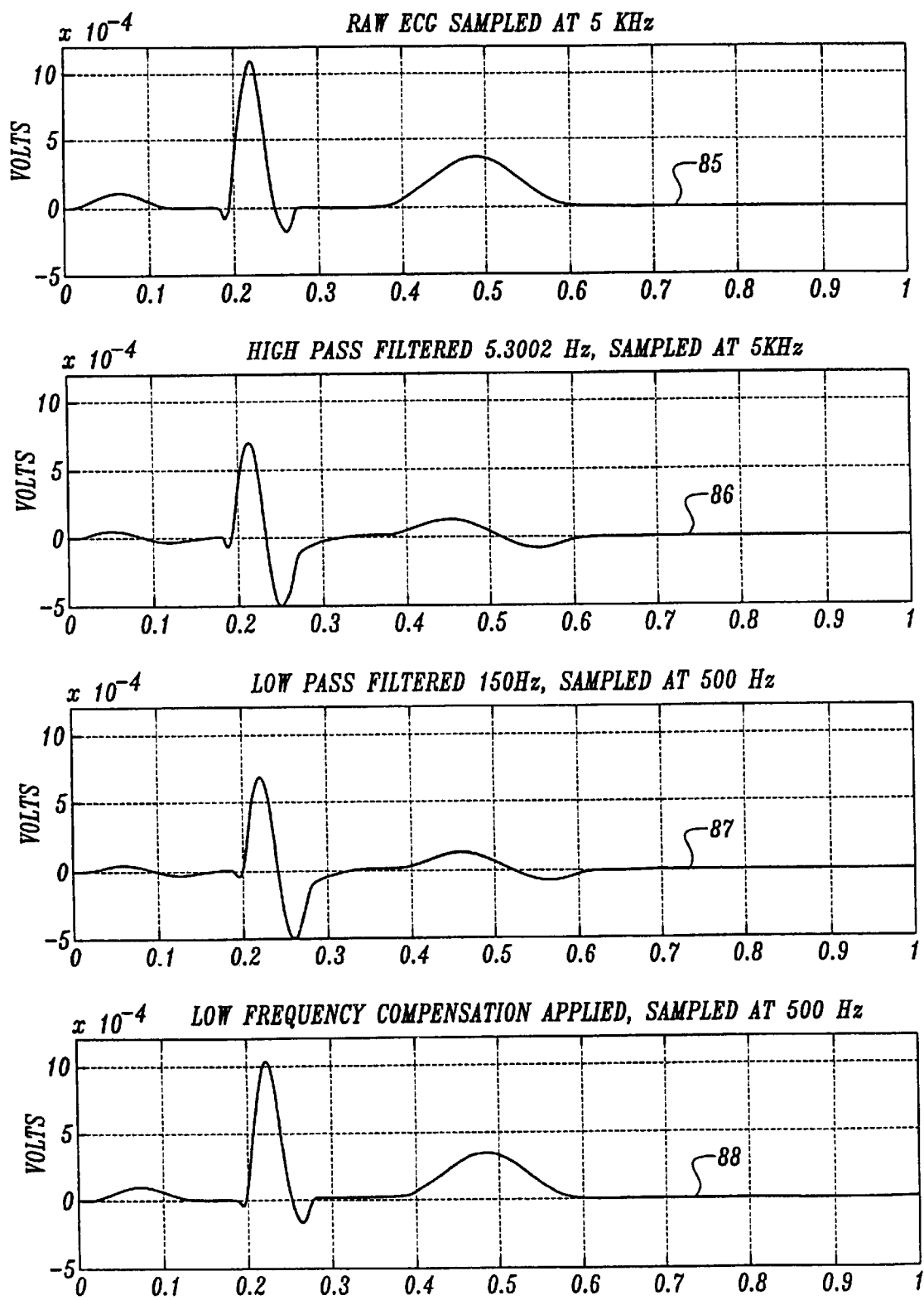
FIG. 10 a graph illustrative of the waveforms generated by the signal measuring system of FIG. 9 with a greater high pass filter corner frequency.

FIG. 10 shows the same waveforms as FIG. 9, but with HPF 42 and matching CF 44 corner frequencies set to 5.3 Hz. This results in even greater droop in intermediate waveforms 86 and 87, the output signals generated from HPF 42 and DF 44 respectively. The output signal generated from CF 46, shown as a waveform 88 has the same fidelity as the output waveform 83 of CF 46, also clearly nearly identical to the raw input waveform 80, maintaining the fidelity required for diagnostic interpretation of the signals.

Figure 11:
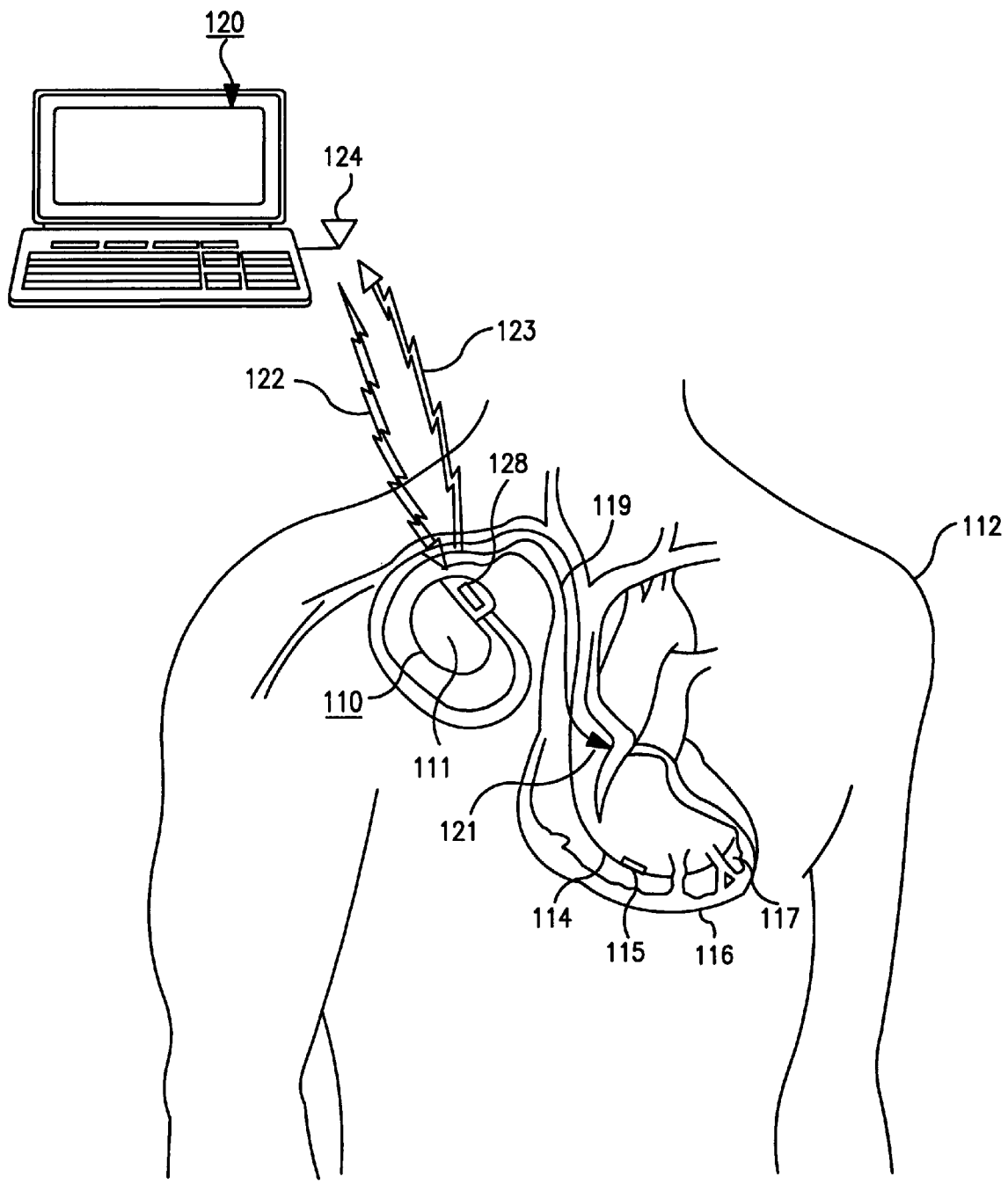
FIG. 11 is a schematic diagram illustrating an exemplary Implantable Medical Device (IMD) of the type that may employ the present invention.

FIG. 11 is a schematic diagram illustrating an exemplary Implantable Medical Device (IMD) of the type that may employ the present invention. The IMD could be a pacing device, a defibrillation device, an implantable loop recorder, a hemodynamic monitor that does not provide a pacing therapy, or any other implantable cardiac therapy delivery device known in the art. In this example, the IMD is an Implantable Pulse Generator IPG 110 implanted in the patient 112. In the illustrated embodiment, IPG 110 is electrically coupled to the heart 116 of the patient 112 through pace/sense electrodes and lead conductor(s) of at least one cardiac pacing lead 119 in a manner known in the art. IPG 110 may further include blood pressure or other physiologic sensors, such as sensor 115 shown provided on the ventricular lead body within the right ventricle.

The IPG 110 may be controlled by an operating system that employs a microcomputer or a digital state machine for timing sensing and pacing functions in accordance with a programmed operating mode. The IPG 110 also contains sense amplifiers for detecting cardiac signals, patient activity sensors or other physiologic sensors for sensing the need for cardiac output, and pulse generating output circuits for delivering pacing pulses to at least one chamber of the heart 116 under control of the operating system in a manner well known in the prior art.

Data signals stored by the IPG are transmitted between an IPG RF telemetry antenna 128 and an external RF telemetry antenna 124 associated with an external programmer 120. In an uplink telemetry transmission 122, the external RF telemetry antenna 124 operates as a telemetry receiver antenna, and the IPG RF telemetry antenna 128 operates as a telemetry transmitter antenna. Conversely, in a downlink telemetry transmission 123, the external RF telemetry antenna 124 operates as a telemetry transmitter antenna, and the IPG RF telemetry antenna 128 operates as a telemetry receiver antenna. Both RF telemetry antennas 124 and 128 are coupled to a transceiver including a transmitter and a receiver.

In the illustrated embodiment, atrial and ventricular pace/sense electrodes 121 and 117 are located at the distal ends of the atrial and ventricular leads 119 and 114, respectively. These leads are positioned in the right atrium and right ventricle, respectively. The electrodes 121 and 117 are shown as unipolar electrodes that are each paired with the conductive housing of the IPG 110 for unipolar pacing and far-field sensing. Alternatively, bipolar electrode pairs may be provided at the distal ends of the atrial and ventricular leads 119 and 114, respectively, for bipolar pacing and near-field sensing.

It will be understood that other leads and pace/sense electrode configurations other than those depicted in FIG. 11 may be used with the current invention. For example, multiple electrodes may be located on, or closely adjacent to, the conductive housing of the IPG 110. This type of an electrode configuration, sometimes referred to as a subcutaneous electrode array, is shown and described in U.S. Pat. No. 5,331,966, assigned to the assignee of the current invention and incorporated herein by reference in its entirety. This type of electrode array is discussed further below.

Figure 12:
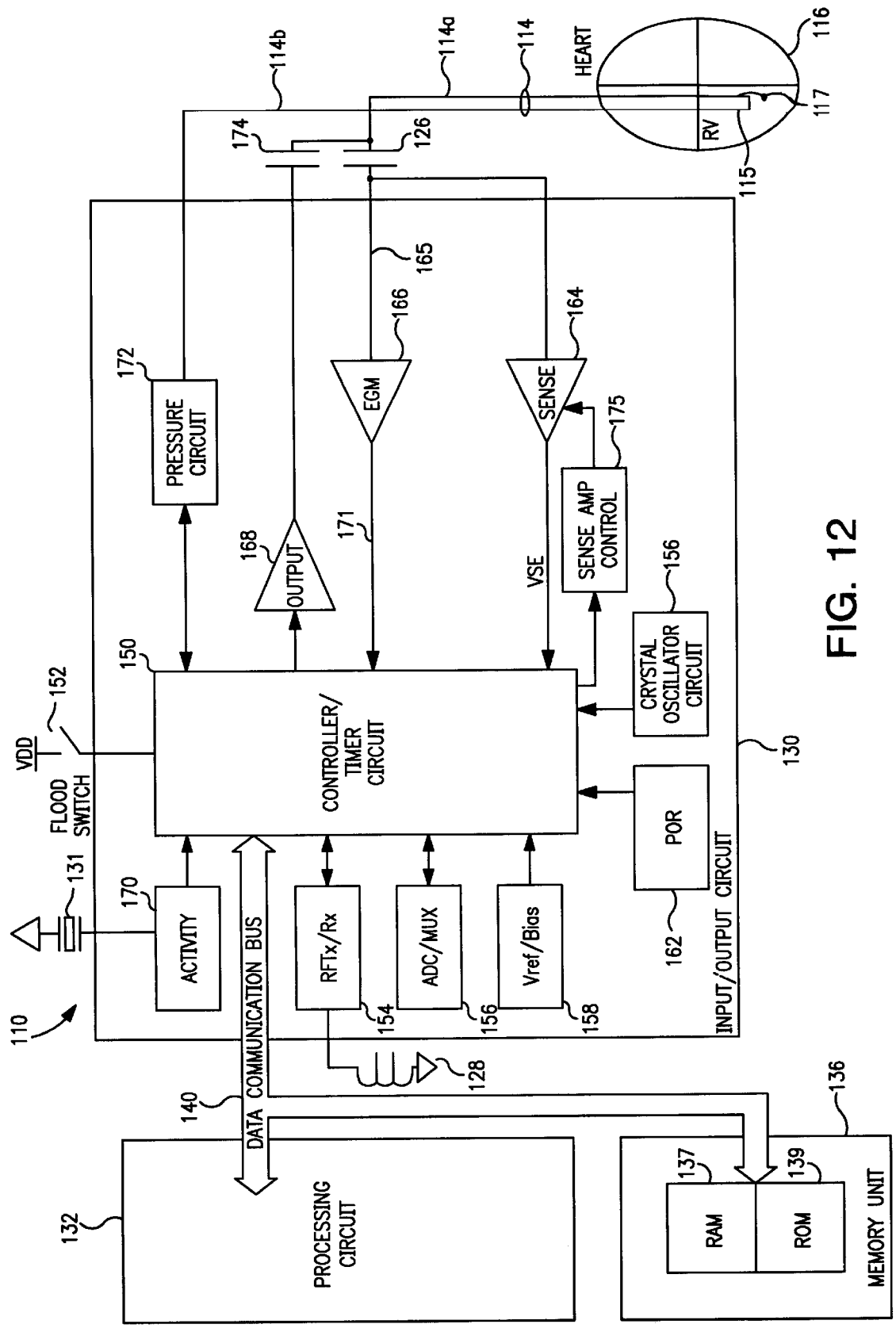
FIG. 12 is a system block diagram illustrating the exemplary IPG discussed in reference to FIG. 11.

FIG. 12 is a system block diagram illustrating the exemplary IPG discussed in reference to FIG. 11. In this diagram, only ventricular lead 14 and the ventricular pacing and sensing channel is depicted, although it will be understood that an atrial pacing and sensing channel may be implemented in substantially the same manner.

IPG 110 includes input/output circuit 130. This circuit contains the analog circuits for processing cardiac signals, and any other signals such as those provided by activity sensor 131 and sensor 115 of lead 114. Input/output circuit 130 further receives the downlink RF telemetry signals received by RF telemetry antenna 128, and provides any pacing pulses to heart 116.

As discussed in reference to FIG. 11, lead 114 may include an electrode placed in the vicinity of heart 116. Lead 114 includes lead conductors 114a and 114b. Lead conductor 114a is coupled via capacitor 126 to sense amplifier 164. The sense amplifier 164 is of conventional design and includes an amplification stage, a peak sense stage, and a threshold measurement stage. Controller/timer circuit 150 controls the gain of amplifier 164 via sensitivity control circuit 175.

Sense amplifier 164 provides a Ventricular Sense Event (VSE) signal indicative of cardiac activity to controller/timer circuit 150. The digital controller/timer circuit 150 employs programmed detection criteria to process the VSE signal. In response to this signal, the control/timer circuit may reset the pacing escape interval, trigger sense event markers, or make a determination of a malignant high heart rate.

Lead conductor 114a may be further coupled to output pulse generator 168 through coupling capacitor 174. Output pulse generator 168 provides pacing pulses to the heart 116 in response to a pacing trigger signal developed by digital controller/timer circuit 150. The pacing trigger signal may be generated each time the escape interval elapses, or when an externally-transmitted pacing command has been received. The trigger signal may also be provided in response to other stored commands as is well known in the pacing art.

Lead conductor 114a is also coupled to EGM circuit 166. According to the invention, EGM circuit 166 includes components similar to those discussed above in reference to FIG. 8. During operation, the signal on net 165 will be provided to a preamplifier 31 as shown in FIGS. 4 or 8. The signal provided by preamplifier circuit 31 will be processed by the other circuit components shown in FIGS. 4 or 8 as discussed above. Assuming all components are implemented in hardware, the output signals of either FIGS. 4 or 8 will be driven onto node 171 of FIG. 12 and to Controller/Timer Circuit 150.

As noted above, DF 44, CF 46 and/or LPF 94 shown in FIGS. 4 and 8 may be implemented in software rather than hardware. If these components are implemented in software or firmware, the signals from ADC 35 may be provided via Controller/Timer Circuit 150 to Data Communication Bus 148. These signals may be stored in Memory Unit 136 to be processed later by Processing Circuit 132 according to a software or firmware program that may also be stored in Memory Unit 136 or an embedded storage device of the Processing Circuit 132. In another embodiment, Processing Circuit 132 can process the signals provided by EGM Circuit 166 in real time without the signals first being stored in Storage Device 136. In yet a further embodiment, these signals may be transferred to programmer 120 via RF telemetry antenna 128 and RF transmitter/receiver 154. Software, firmware, hardware, or any combination of the foregoing may be included within programmer to implement the DF 44, CF 46, and LPF 94 components.

Signals received by the Controller/Timer Circuit may be transferred to programmer 120 via the RF telemetry antenna 128 during real time uplink telemetry. This is as described in commonly-assigned U.S. Pat. No. 4,556,063, incorporated herein by reference in its entirety.

Lead conductor 114b extends from sensor 115, which in this example is a pressure sensor, to a pressure signal processing circuit 172 of the type described in the above incorporated '040, '434, and '752 patents. Pressure signal processing circuit 172 may receive, amplify, and process a signal received from sensor 115, which may, in turn, provide this signal indicative of cardiac pressure to controller/timer circuit 150. This value may be transferred to external programmer 120, or stored in memory unit 136. In one embodiment, the system and method of the current invention could be used to process signals received from sensor 115.

Input/output circuit 130 is coupled through a data communications bus 148 and control lines (not shown) to a processing circuit 132 such as a microprocessor. Processing circuit provides the controller/timer circuit 150 with commands for controlling the timing of IPG 110. For example, these commands establish the overall pacing escape interval, as well as various refractory, blanking, and other timing windows for controlling the operation of the peripheral components within input/output circuit 130.

Input/output circuit 130 may further be coupled to memory unit 136, which generally includes RAM 137 and/or ROM 139. Digitized measurements provided by EGM circuit 166 may be stored in memory unit 136 temporarily until being transferred to programmer 120 via the RF telemetry antenna 128, or alternatively may be transferred directly to the programmer. Memory unit may further store other data signals, programming instructions, and operation parameters that may be needed by the system.

Input/output circuit 130 may be coupled to an activity sensor 131. This may be a piezoelectric element bonded to the inside of the housing of the IPG, or may be another type of activity sensor. Activity sensor 131 provides a signal indicative of patient activity levels to activity signal processor 170, which, in turn, provides a signal to controller/timer circuit 150. Controller/timer circuit 150 responds to this signal by adjusting the pacing rate to meet the metabolic requirements of the patient in a manner well known in the art.

The RF telemetry antenna 128 is coupled to controller/timer circuit 150 via RF transmitter/receiver 154 for purposes of performing uplink/downlink telemetry. Both analog and digital data may be transferred between antenna 128 and antenna 124 of FIG. 11. An uplink telemetry transmission of real time and stored data may be initiated when programmer 120 provides an interrogation command to IPG 110. Telemetry transmissions may be accomplished by employing any of the RF telemetry encoding schemes known in the art.

A reed switch 152 may also be coupled to the digital controller/timer circuit 150. The reed switch 152 may be placed in a predetermined position upon the creation of a magnetic field in the vicinity of the implanted IPG. The switch position may be employed to alter the operating mode of IPG 110, or to enable uplink and downlink telemetry in a manner well known in the art.

Several other circuits are shown coupled to digital controller/timer circuit 150. A crystal oscillator circuit 156 provides clock signals to controller/timer circuit 150. A Vref/Bias circuit 158 generates a stable voltage reference and bias currents for the analog circuits of input/output circuit 130. An analog-to-digital converter/multiplexor (ADC/MUX) unit 160 digitizes analog signals and voltages for storage in RAM, and may provide "real-time" telemetry of pressure and intracardiac signals. ADC/MUX may also provide the battery End-Of-Life (EOL) replacement function. A Power-On-Reset (POR) circuit 162 provides reset circuitry to cause IMD to enter a default condition upon detection of a low battery condition, as will occur upon device power-up, or as may occur in the presence of electromagnetic interference.

It will be understood that the above-described IPG configuration shown in FIG. 12 is exemplary only. The current invention may be used with an IPG having one or more of the various components shown in FIG. 12.

As discussed above, the current invention need not be used only in conjunction with electrodes located on pacing leads placed within the heart or cardiac vasculature. The invention may also be used in conjunction with an IMD including one or more subcutaneous electrodes located on, or closely adjacemt to, the case of the IMD. These electrodes may sense far-field EMG signals as discussed in U.S. Pat. No. 5,331,966 referenced above. The electrodes may be electrically isolated from one another and the conductive surface of the IMD through suitable insulation material, and are coupled to internal circuitry using conductive feedthroughs. The signal provided by each subcutaneous electrode could be processed by an associated EGM circuit 166 of the type discussed above in reference to FIGS. 12 and 8. Alternatively, multiple electrodes could be coupled through a switching circuit so that one EGM circuit processes multiple signals sequentially.

FIGS. 13A through 13E are diagrams illustrating various configurations of subcutaneous electrodes positioned adjacent to the housing of an IMD 200. In one embodiment, the spacing of the electrodes A, B and C on each of the illustrated orientations is about one inch. This distance may be larger or smaller depending on the size of the device.

FIG. 13A illustrates orthogonally disposed electrodes A, B, and C. Electrodes A and B are located on a connector block 202, and electrode C is located on the case 204 of IMD. FIGS. 13B and 13C illustrate embodiments wherein at least one of the electrodes extends away from the IMD. In FIG. 13B, the electrode B is positioned on a stubby lead extension 206, and in FIG. 13C, electrode B is positioned on the lead 208 to provide a greater inter-electrode spacing.

FIGS. 13C and 13D illustrate embodiments wherein the relative orientation of the electrodes may vary from the orthogonal orientation shown in FIGS. 13A and 13B. Additionally, FIG. 13D shows electrodes A, B, and C positioned adjacent to the sides of the IMD 200. In FIG. 13E, the electrodes A and B are adjacent to the case 204 of the IMD, whereas only electrode C is located on a connector block 202.

As noted above, conventional signal measuring systems utilized by Implantable Medical Devices modify waveform morphology. This makes it difficult to diagnose conditions such as ischemia.

Figure 14A:
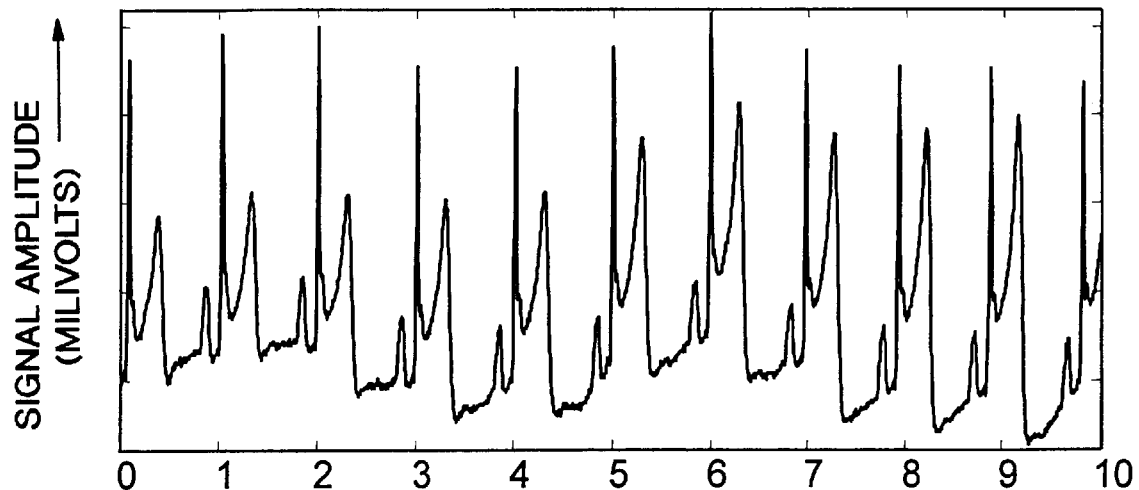
FIG. 14A is a timing diagram of a typical ECG waveform during an ischemic episode.

FIG. 14A is a timing diagram of a typical ECG waveform during an ischemic episode. As may be noted, the QRS complex is lengthened in a tell-tale manner. This waveform morphology is an important characteristic used in diagnosing this condition.

Figure 14B:
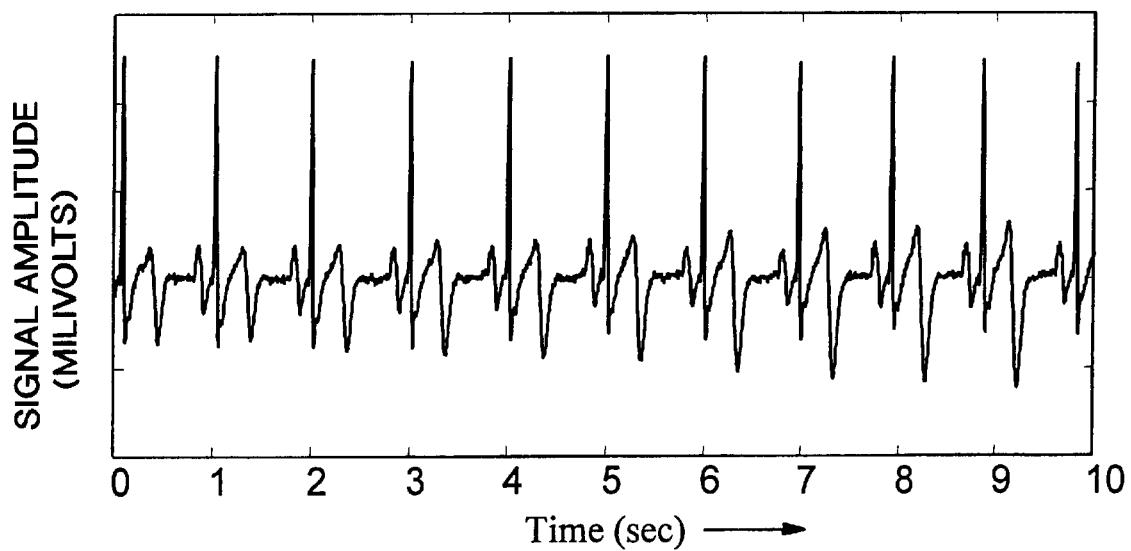
FIG. 14B is a timing diagram illustrating an ECG waveform that has been filtered using a prior art system and method such that the morphology is not indicative of ischemia.

FIG. 14B is a timing diagram illustrating measurement of the same signal measured in FIG. 14A, however the morphology is not indicative of ischemia. This is because the signal has been filtered using a conventional measuring system of the type generally included within an IMD. This filtering largely removes the characteristics used to identify ischmia, making the diagnosis is difficult if not impossible.

The current invention provides a system and method for measuring signals without changing the waveform morphology in this manner. For example, the current system is capable of generating a signal that includes the waveform changes exemplified in FIG. 14A so that ischemia can be readily detected and treated. These signals can then be processed using an ischemia detection system of the type described in commonly assigned U.S. Pat. No. 6,128,526 granted Oct. 3, 2000 entitled "Method for Ischemia Detection and Apparatus for Using the Same", incorporated herein by referenced in its entirety. Other ischemia detection systems and methods may alternatively be used to perform the ischemia detection, such as those described in commonly-assigned U.S. patent application Ser. No. 09/280,286 first filed Mar. 29, 1999 entitled "Improved Method for Ischemia Detection and Apparatus for Using the Same", and commonly-assigned U.S. patent application Ser. No. 09/407,602 first filed Mar. 29, 1999 entitled "Ischemia Detection During Non-Standard Cardiac Excitation Patterns", both incorporated herein by reference in their entirety.

One skilled in the art may comprehend many additional configurations of subcutaneous electrodes that may comprise more or fewer electrodes positioned in different spacings and orientations.

The embodiments of the signal measuring system for Implantable Medical Devices described above are illustrative of the principles of the present invention and are not intended to limit the invention to the particular embodiments described. For example, in light of the present disclosure, those skilled in the art can devise an embodiment of the present invention included within an IMD for measurement of other than cardiac signals. Such a system is readily adaptable to measure physiological signals in any situation in which large amplitude, low-frequency, non-physiological signals can result in loss of physiologic signal information. Additionally, embodiments using different implementations of the CF or different dither signals may be devised. Those skilled in the art, in light of the present disclosure, can adjust the sampling rate and decimation ratio to accommodate different output signal frequency bandwidths and low-end bands. Accordingly, while the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for use by an Implantable Medical Device (IMD) of filtering a physiological signal having a predetermined frequency bandwidth, the method comprising:
   obtaining the physiological signal from a sensor coupled to the IMD;
   filtering the physiologic signal with a high pass filter (HPF), the cutoff frequency of the HPF being within the predetermined frequency bandwidth, wherein a low-band portion of the predetermined frequency bandwidth is attenuated;
   sampling an output signal from the UPF to generate a stream of samples with a predetermined sample rate greater than twice the upper frequency of the predetermined frequency bandwidth; and
   filtering the stream of samples with a compensation filter (CF), wherein the CF provides a gain for the low-band portion that is substantially equal to the inverse of the attenuation of the low-band portion; and
   decimating the stream of samples.

2. The method of claim 1 wherein the filtering of the stream of samples with the CF is implemented using programmed instructions.

3. The method of claim 2, wherein the programmed instructions are executed on a processing circuit included within the IMD.

4. The method of claim 2, wherein the programmed instructions are executed on a processing circuit located external to the IMD.

5. The method of claim 1 further comprising decimating the stream of samples.

6. The method of claim 1 further comprising combining a known dither signal with the filtered physiological signal.

7. The method of claim 6 wherein the dither signal has a dynamic range at least as great as the resolution of each sample of the stream of samples.

8. The method of claim 1 further comprising combining a known dither signal with the physiological signal.

9. The method of claim 1 wherein the predetermined frequency bandwidth ranges from about 0.05 Hz to about 100 Hz.

10. The method of claim 9 wherein the sample rate of the sampling method is about 256 samples per second.

11. The method of claim 1, wherein the obtaining method obtains the physiological signal using at least two electrodes located adjacent to a casing of the IMD.

12. The method of claim 1, wherein the obtaining method obtains the physiological signal using at least one electrode located on an implanted lead coupled to the IMD.

13. The method of claim 1, and further including filtering the physiological signal with an anti-aliasing filter.

14. A filter system for an Implantable Medical Device (IMD) for use in generating an output signal having a predetermined frequency bandwidth in response to a sensed signal from a patient, the system comprising:
   a high pass filter (HPF) having a cutoff frequency within the predetermined frequency bandwidth, wherein the HPF is configured to attenuate a low-band portion of the predetermined frequency bandwidth;
   an analog-to-digital converter (ADC) coupled to the RIPF, the ADC being configured to generate a stream of samples with a predetermined sample rate greater than twice the upper frequency of the predetermined frequency bandwidth; and
   a compensation filter (CF) coupled to the ADC, wherein the CF is configured to provide a gain for the low-band portion that is substantially equal to the inverse of the attenuation of the low-band portion; and
   a decimator coupled to the CF.

15. The system of claim 14, wherein the CF comprises a processing circuit to execute programmed instructions implementing a digital filter.

16. The system of claim 15, wherein the processing circuit is located within the IMD.

17. The system of claim 15, wherein the processing circuit is located external to the IMD.

18. The system of claim 14 further comprising a decimator coupled to the CF.

19. The system of claim 14 further comprising a dither generator circuit coupled to the HPF configured to combine a known dither signal with the sensed signal.

20. The system of claim 19 wherein the dither signal has a dynamic range at least as great as the resolution of each sample of the stream of samples.

21. The system of claim 14 wherein the predetermined frequency bandwidth ranges from about 0.05 Hz to about 100 Hz.

22. The system of claim 21 wherein the sample rate is about 256 samples per second.

23. The system of claim 22 wherein the HPF is implemented in hardware.

24. The system of claim 14, and further comprising at least two electrodes coupled to provide the sensed signal to the HPF.

25. The system of claim 24, wherein at least one of the two electrodes is carried on an implantable lead.

26. The system of claim 24, wherein at least one of the two the electrodes is located adjacent to housing of the IMD.

27. The system of claim 14, and further including an anti-aliasing filter coupled to the HPF to receive the sensed signal from the patient, and to provide a filtered signal to the HPF.

28. A system for use with an Implantable Medical Device (IMD) in generating an output signal having a predetermined frequency bandwidth in response to a sensed signal from a patient, the system comprising:
   a high pass filter (HPF) coupled to the anti-aliasing filter, the HPF having a cutoff frequency within the predetermined frequency bandwidth, wherein the HPF is configured to attenuate a low-band portion of the predetermined frequency bandwidth;
   an analog-to-digital converter (ADC) coupled to the HPF, the ADC being configured to generate a stream of samples with a predetermined sample rate greater than twice the upper frequency of the predetermined frequency bandwidth; and
   compensation means coupled to the ADC, for digitally filtering the stream of samples, wherein the compensation means is configured to provide a gain for the low-band portion that is substantially equal to the inverse of the attenuation of the low-band portion; and
   decimation means coupled to the compensation means.

29. The system of claim 28, wherein the compensation means includes storage means for storing programmed instructions, and processing means for executing the programmed instructions to digitally filter the stream of samples.

30. The system of claim 29, wherein the processing means is included within the Implantable Medical Device.

31. The system of claim 29, wherein the processing means is external to the Implantable Medical Device.

32. The system of claim 28 further comprising decimating the stream of samples.

33. The system of claim 28 further comprising a dither generator circuit configured to combine a known dither signal with the output signal from the HPF.

34. The system of claim 33 wherein the dither signal has a dynamic range at least as great as the resolution of each sample of the stream of samples.

35. A filter system for use in generating an output signal in response to a physiological signal sensed from a patient, the output signal having a predetermined frequency bandwidth, the filter system comprising:
- at least two electrodes located within the patient and configured to provide a sensed signal in response to the physiological signal;
- a high pass filter (HPF) located with the patient and coupled to receive the sensed signal, the HPF having a cutoff frequency within the predetermined frequency bandwidth, wherein the HPF is configured to attenuate a low-band portion of the predetermined frequency bandwidth;
- an analog-to-digital converter (ADC) coupled to the HPF, the ADC being configured to generate a stream of samples with a predetermined sample rate greater than twice the upper frequency of the predetermined frequency bandwidth; and
- a compensation filter (CF) coupled to receive the stream of samples, and to generate an output signal wherein the low-band portion with a gain that is substantially equal to the inverse of the attenuation of the low-band portion; and
- a decimator coupled to the CF.

36. The system of claim 35, wherein the CF comprises a processing circuit and a storage device coupled to the processing circuit, the processing circuit to execute programmed instructions stored in the storage device to generate the output signal.

37. The system of claim 36, and further including a programmer external to the patient that includes the CF, and a telemetry antenna coupled to the ADC to receive the stream of samples, and to transfer the stream of samples to the programmer to be processed by the CF.

38. The system of claim 36 wherein the CF is located within the patient.

39. The system of claim 35, and further including a storage device coupled to receive and to store the output signals.

40. The system of claim 35, and further comprising a decimator coupled to the CF.

41. The system of claim 35, and further comprising a dither generator circuit coupled to the HPF and configured to combine a known dither signal with a signal provided by the HPF.

42. The system of claim 35, and further comprising a dither generator circuit coupled to the HPF and configured to combine a known dither signal with the sensed signal provided to the HPF.

43. The system of claim 41, wherein the dither signal has a dynamic range at least as great as the resolution of each sample of the stream of samples.

* * * * *

UNITED STATES PATENT AND TRADEMARK OFFICE
CERTIFICATE OF CORRECTION

PATENT NO.    : 6,316,575 B1
DATED         : November 13, 2001
INVENTOR(S)   : Kuze et al.

It is certified that error appears in the above-identified patent and that said Letters Patent is hereby corrected as shown below:

<u>Title page,</u>
Item [56], References Cited, FOREIGN PATENT DOCUMENTS, please add the following:

```
--   7-620074    03/1995    (JP)
     7-260010    01/1995    (JP)
     7-247354    09/1995    (JP)
     7-109346    04/1995    (JP)
     9-157383    06/1997    (JP) --
```

Signed and Sealed this

Twenty-fourth Day of December, 2002

JAMES E. ROGAN
*Director of the United States Patent and Trademark Office*